US006877358B2

(12) United States Patent
Beckwith

(10) Patent No.: US 6,877,358 B2
(45) Date of Patent: Apr. 12, 2005

(54) PROGRAMMABLE APPARATUS USING MOLECULAR RESONANCES FOR MEASURING PARTICLES SUSPENDED IN AIR

(76) Inventor: Robert W. Beckwith, 2794 Camden Rd., Clearwater, FL (US) 33759

( * ) Notice: Subject to any disclaimer, the term of this patent is extended or adjusted under 35 U.S.C. 154(b) by 102 days.

(21) Appl. No.: 10/607,403

(22) Filed: Jun. 26, 2003

(65) Prior Publication Data

US 2004/0003649 A1 Jan. 8, 2004

Related U.S. Application Data

(60) Provisional application No. 60/394,419, filed on Jul. 8, 2002.

(51) Int. Cl.[7] .................................... G01N 29/02
(52) U.S. Cl. .................................... 73/24.06
(58) Field of Search .................................... 73/23.2, 23.3, 73/23.32, 23.33, 23.34, 24.06, 335.03, 335.04, 335.05; 324/464, 633

(56) References Cited

U.S. PATENT DOCUMENTS

| | | | | | |
|---|---|---|---|---|---|
| 4,132,943 | A | * | 1/1979 | Gournay et al. | 324/335 |
| 4,385,516 | A | * | 5/1983 | Uffelman | 73/24.01 |
| 4,536,713 | A | * | 8/1985 | Davis et al. | 324/324 |
| 5,126,672 | A | * | 6/1992 | Le Roux | 324/309 |
| 5,503,133 | A | * | 4/1996 | Trigger | 123/637 |
| 5,744,970 | A | * | 4/1998 | Kim et al. | 324/636 |
| 5,918,257 | A | * | 6/1999 | Mifsud et al. | 73/23.34 |
| 6,052,183 | A | * | 4/2000 | Lee | 356/337 |
| 6,359,444 | B1 | * | 3/2002 | Grimes | 324/633 |

* cited by examiner

*Primary Examiner*—Charles Garber
(74) *Attorney, Agent, or Firm*—Leo J. Aubel

(57) ABSTRACT

A programmable device for analyzing mixtures of suspended vapors and air by pinging particles making up the vapors at their mechanical resonant frequencies and detecting the resultant rings.

5 Claims, 3 Drawing Sheets

Side view

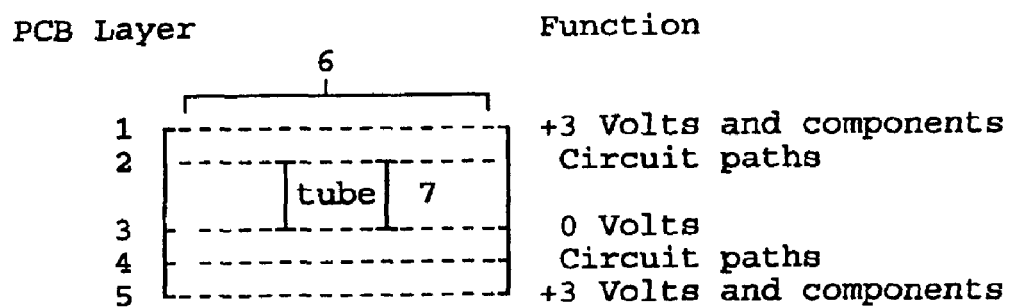
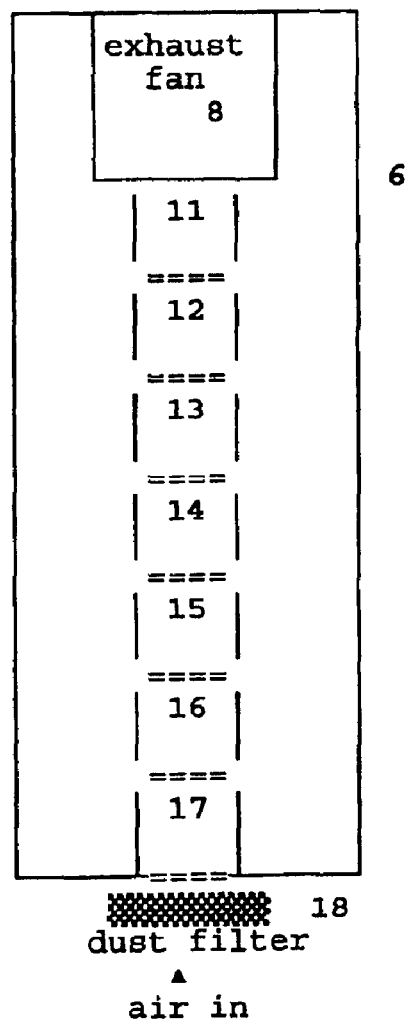
Fig. 1  Top view  (-------- is PCB foil)
Fig. 2  Side view

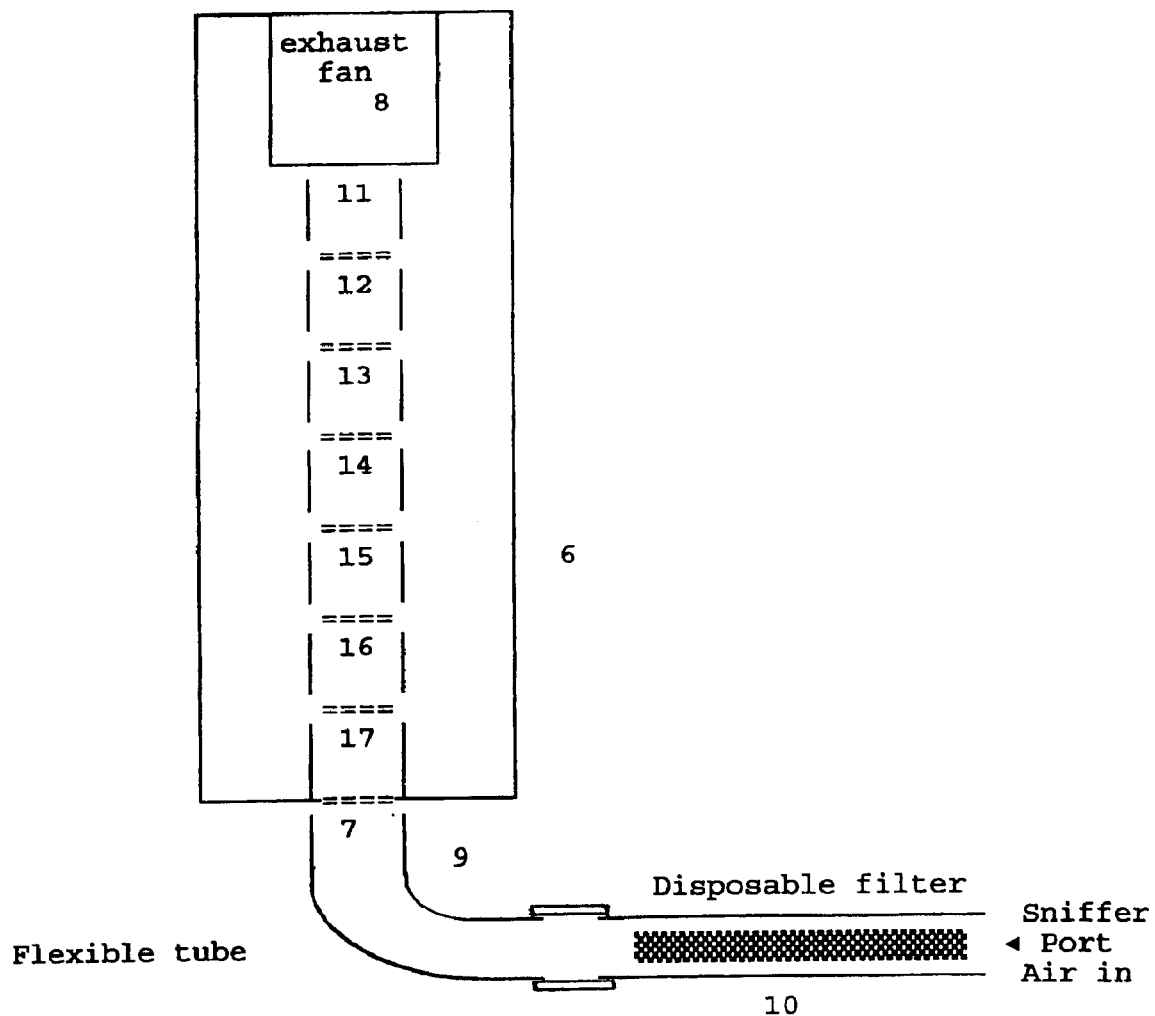
Fig. 3, Device for locating land mines.

PCB Layer                Function
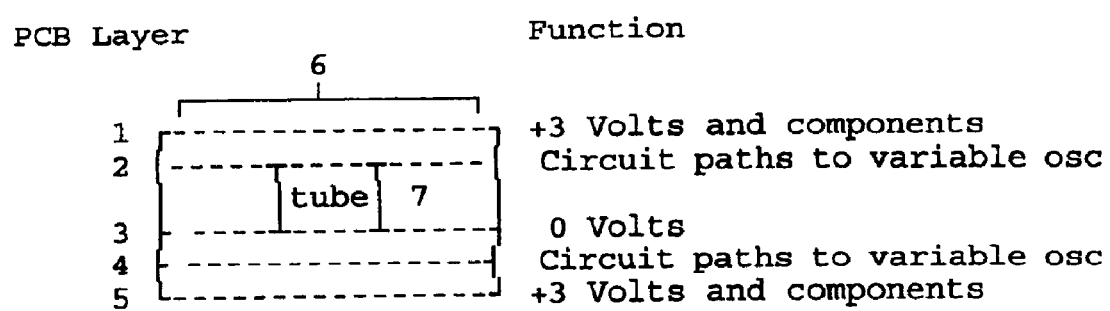
| | |
|---|---|
| 1 | +3 Volts and components |
| 2 | Circuit paths to variable osc |
| 3 | 0 Volts |
| 4 | Circuit paths to variable osc |
| 5 | +3 Volts and components |
Fig. 4a   Top view (- - - - - - - -  is PCB foil)
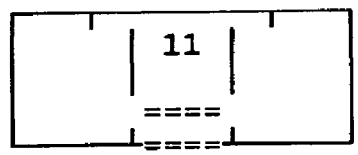
Fig. 4b   Side view

US 6,877,358 B2

PROGRAMMABLE APPARATUS USING MOLECULAR RESONANCES FOR MEASURING PARTICLES SUSPENDED IN AIR

This patent application claims the date of provisional patent application No. 60/394,419 filed on Jul. 8, 2002.

BACKGROUND OF THE INVENTION

Engineers from Sandia Laboratory have started a company, MicroChemLab Technologies, to use a patented chip known as "a chem lab on a chip". This device has a surface with divided areas that identify a choice spectrum of molecules expected to be associated with minuscule amounts of breath vapors, fluids and tissues to detect infections and biological warfare agents. A hand held scanner does diagnostic work in seconds. The chip has a useful life of about six months after which time it must be replaced.

Another briefcase sized device has been described in public meetings which is said to be capable of mapping gold on or near the surface of the earth from an airplane flying at 5000 feet elevation. This is described as sending a ping at the resonant frequency of gold, cutting the ping off at a zero crossing and detecting the ring of the gold atoms. The results are plotted on a map of the ground and displayed on a computer used as a part of the device. Details are not made available in the lectures but an offer is made to survey your property at a rather large fee. The lecturer claims that much of the gold found is buried treasure! A patent, if one has been granted, will be listed below as a reference.

References

1. U.S. Pat. No. 5,544,064 APPARATUS AND METHOD FOR SAMPLING SIGNALS SYNCHRONOUS WITH ANALOG TO DIGITAL CONVERTER by Robert W. Beckwith the inventer herein.

SUMMARY OF THE INVENTION

Particles are defined as including atoms, molecules, dust particles, small balls of water and other vapors that may become suspended in the atmosphere for some considerable time. Generally the particles are held apart in suspension by negative charges on each particle.

The inventive devices "sniff" the atmosphere containing particles of interest using small fans or other means of causing a flow of atmosphere through the devices. The flow is caused to be laminar by a void created in an inner layer of a multilayered printed circuit board. The width of the void is large as compared to the thickness of the void thus minimizing turbulence in the air as it passes through the devices.

The void is divided lengthwise into segments measuring a number of particles of interest where the number that can be measured equals the number N of segments.

Each segment has a common conducting surface along one side of the void and isolated surfaces on the opposing surfaces each forming a measuring segment. The isolated surfaces are electrically insulated from each other. Each segment is "pinged" by a brief oscillating voltage from an isolated surface to the common surface. This causes any particles suspended in the air passing through the void to ring as a bell for some short time immediately after being pinged. The ring is measured by receiving circuits switched on immediately following a ping. The magnitude of the ring uses a first cross-correlation between digital samples of the ring voltage and tables of sine and cosine functions. The magnitude of the ring is a measure of the concentration of particles of interest.

The measurement of particles is resolved as a frequency spectrum over the band of N frequencies which include the resonances of particles of interest. A second cross-correlation is made between the N measurement and tables of sine and cosine functions resolved to N values each. This result is called the odor of the sample. The tables may include values for several similar odors permitting a readout of the probability of each odor being in the sample of air that is sniffed.

Voltage controlled oscillators are used on the printed circuit board to establish frequencies corresponding to selected particles. The frequency controlling voltages are held by capacitors so as to implement programming the devices for a selected number of particles. The voltages are set into the capacitors by a programming device not otherwise described herein.

Preferably the results are telemetered to a monitoring location using Beckwith Electric BLUEJAY™ wireless devices.

BRIEF DESCRIPTION OF THE DRAWINGS

FIG. 1 A cross section of the printed circuit used in the device. Note that the scale through the board is exaggerated for clarity.

FIG. 2 A view of the device when configured for carrying on a person when in a hazardous area.

FIG. 3 A view of the device configured with a flexible tube attached as when used to "sniff" for a land mine.

FIG. 4 A single element device useful for measuring the resonant frequency of a known gas.

DESCRIPTION OF THE PREFERRED EMBODIMENTS

Particles are defined as including atoms, molecules, dust particles, small balls of water and other particles that may form a vapor by becoming suspended in air for some considerable time. Generally the particles are held apart in an air suspension by negative charges on each particle thus forming a vapor. Odors, as used herein, refer to vapors that may be sensed by humans and certain animals as a smell.

Some odors could indicate the presence of an explosive device or air mixture. Other odors might indicate the presence of a perfume that might be significant in a crime scene. Some vapors of interest may have no odor. One such example is carbon monoxide, well known to be dangerous to breath.

This invention provides for detecting a number N of particles that may be programmed for detection for any immediate use of a general purpose vapor analyzing device. The number N is determined by the specific design of an inventive device as described in more detail hereinunder.

The resonance of a particle of interest, be it an atom, a molecule or a particle of dust or a mist can be thought of as a mechanical resonance. Each of the particles are held apart by an electric charge (usually negative) when suspended in a mixture with air. Devices under the present invention use this charge to excite (ping) the particles with an electric wave across a thin void in a circuit board. The particles then ring like a bell giving back the expected ring signal.

Vapors are analyzed in a tube formed by a void in an internal layer of a multi-layered printed circuit board (PCB).

Vapors (air/particular mixtures) are drawn into the PCB void through a filter to remove particles of dust larger than the size the filter is designed to pass.

A selected number N of foil segments along a first side of the tube are excited with voltage waves at particular resonant frequencies for each particle for which the device is programmed to detect. A solid foil over the second side of the PCB tube forms a common circuit ground return for the voltage waves. Frequencies are derived from voltage controlled oscillators and first used to drive the ping and then to drive a cross-correlation multiplier to detects the ring. Immediately after the ping, the resulting ring of the particle is detected by taking digital samples at the ping frequency of any voltage wave that is picked up by the foil segment. These samples are multiplied by tables of sine and cosine functions. The cross correlation thus obtained gives the probability of the existence of the particle programmed to each foil segment, in other words the concentration of that particle in the air sample. Use of both a sine and a cosine table also gives the time offset that may exist between the ping and the ring.

Methods of obtaining cross correlations and time offsets by multiplying samples of a time wave by sine and cosine tables in a synchronous manner are disclosed in reference 1 U.S. Pat. No. 5,544,064.

Cross correlations are averaged over a time ▲t required for a particle to pass over a measuring segment. The results are placed in a file. At the end of each time ▲t a second digital cross-correlation is made by multiplying each member of the file of N results by a table of the expected results for a vapor of interest. Several tables for similar vapors may be included permitting computation of the probable presence of each member of the family of similar vapors.

Selectively data readout is by a display on the device or by a program on an associated computer. Selectively data is communicated to an associated computer by wireless means preferably using Beckwith Electric BLUEJAY™ wireless products.

Intuitively, if it is possible to detect a very large number of gold atoms from an airplane flying 1000 feet above the ground it should be possible to detect a much smaller number of particles in the inventive device at distances of, say 0.01 inches. The distance factor should vary as the cube of the distance.

1: 1000 feet=12,000 inches

2: $(12{,}000/0.01)^3=1.728\times10^{18}$

If one avoirdupois ounce of gold can be detected at 1000 feet and an ounce of gold contains $8.66\times10^{22}$ atoms, 1. then $(8.66\times10^{22})/(1.728\times10^{18}=50{,}000$ particles that should be detectable by the explosive device and if each particle had the weight of a single atom of gold or $0.12\times10^{-22}$ oz.

If the void through the device were ½"×½" in size and thickness 0.01" then the detectable concentration is 50,000/(½×½×0.01)=20 million particles per cubic inch of air.

If the particles were suspended balls of water, then the weight of water in a cubic inch would be $$20\times10^{6}\times0.12\times10^{-22}=2.4\times10^{-16}\text{ oz.}$$

Water weighs 0.6 oz per cubic inch, then the detectable concentration of water vapor is $(2.4\times10^{-16}$ oz)/0.6=4%.

Apparatus for detecting odors uses a small fan located on a printed circuit board (PCB) to pull air through a tube formed in a central layer of the PCB. In a restricted space with dimensions of, say 0.01×0.5 inches, the air flow should be laminar and have minimal energy loss. Flow rates of 10 inches per second are expected. With 1000 pings per second and sampling areas 0.5×0.5 inches, molecules will be sampled 500 times as they pass through each sampling area.

While the suggested ratio of width to thickness of 50 for the void in the PCB is expected to smooth turbulence in the gas/air mixture passing through the inventive device, more smoothing may be obtained by placing a fixed magnetic field across the void. This may align the spin axes of the particles and further reduce the turbulence.

By incorporating a sampling area for each particle which corresponds to two or more odors the device is useful for detecting more than one odor and for determining the mix between two or more.

In a first application the device is for carrying on ones body. An PCB mounted vibrator informs the wearer of the device of the presence of dangerous elements. Selectively a PCB mounted display shows the type of odor found.

In one application a tube from the end of the tube pulls air through a replaceable dust filter thereby forming a land mine odor sniffer. Preferably data is sent by wireless means from one or more robotic sniffers to a computer where analysis is completed and presence of a mine made known to a operator situated a safe distance from a mine field. The robots can be accurately tracked from satellites using GPS positioning. The robots can carry explosive devices designed to blow up the mines. With existing worldwide military communications, the clearing of mine fields can be directed from a central location for any mine field on earth with loss only of robotic sniffers. A measure of success will be the number of mines destroyed by each robot deployed.

Readily available components are located on the PCB to form ping voltages on segments along the tube of one foil layer. Solid foil along an adjoining layer form a zero voltage reference for the pulsed ping voltages.

In a measurement segment of the device each segment of foil is pinged at an assigned resonant frequency to detect a particular particle expected to be found.

FIG. 1 shows a mechanical layout of the inventive apparatus. FIG. 1 is a cross section of the PCB 6 at any location from the bottom of the board to the location of the exhaust fan 8 as shown in FIG. 2 on the upper part of the PCB 6. FIG. 1 is with the thickness of the board greatly exaggerated in order to clearly identify the various foil layers 1, 2, 3, 4, and 5 and the location of a tube 7 formed by removing a section of an inner layer of the PCB. PCB layer 1 carries +3 Vdc to circuit components and is as solid as possible around electrical components so as to form an electrostatic shield around the components. Foil paths on PCB 6 layer 2 caries active circuit connections between components so as to take advantage of the shielding of layer 1. PCB 6 layer 3 carries a zero voltage reference for circuits except for a series of insulated segments 11, 12, 13, 14, 15, 16, and 17 along the air tube 7. PCB 6 layer 4 carries circuit paths and PCB 6 layer 5 carries +3 Volts and electrical components. A dust filter 18 is located at the air intake of tube 7. A compartment, not shown, can be added to carry two disposable 1.5 Vdc batteries as is common for hand carried battery operated devices.

Each detection segment carries the ping voltage and the atomic/molecular ring detected immediately after each ping. The atomic and molecular resonant frequency are expected to be in the gigahertz region. The number of cycles for the ping and for measuring the ring is made variable until data is collected as to optimum number of cycles. Pings and ring measurements are done without pause except for high speed data management. With an air flow through the tube of, say one foot per second, the number of measurements averaged as each atom or molecule passes under each insulated segment is very large.

The time for air passage through the PCB tube 7 is calculated and the vapor identification computed once per passage time. A pause in the measurement cycle is allowed for the identification. With a 10 inch tube in a PCB with 20 sensing segments, three identifications per second is possible at an air flow rate of 30 inches per second.

FIG. 3 shows a device configured to sniff for land mines. The removal of material forms a tube 7 through the PCB 6 for a fan 8 to draw air through the tube 7 and through an external flexible tube 9 used to form a sniffer. The sniffer has a replaceable air filter 10 at the sniffing end. This is the size of a cigarette and uses the same material as in the ends of filter tip cigarettes. This results in a very low cost for the air filters.

FIG. 4 shows a single detection cell device useful for finding the resonant frequency of known vapors sensed one at a time. In a laboratory environment, known vapors are mixed with dry air in controlled percentages. A variable frequency oscillator drives amplifiers creating signals equivalent to those used in devices shown in FIGS. 1, 2 and 3. The frequency of the oscillator is varied to find the frequency of maximum detection sensitivity. This single cell device will also be useful in optimizing the technology of this invention. The resultant frequencies and technology are then used in designing the inventive device described in FIGS. 1, 2, and 3.

While it is assumed that the resonant frequency of atoms and molecules is relatively independent of temperature, the actual dependency can be measured in the laboratory by varying the temperature of the air with which the gas to be detected is mixed.

ADVANTAGES OF THE INVENTION

1—The expected low cost makes the device inexpensive for personal use, and in such locations as airports and building entrances.

2—The expected low cost makes the device expendable for military use when combined with a low cost robotic carrier through a mine field.

3—Mine fields can be cleared with no danger to personnel from mine explosions.

What is claimed is:

1. A device for measuring amounts of selected vapors mixed with air comprising in combination:
   a) A multilayered printed circuit board means having a void along an inner layer for air with vapors to pass through,
   b) fan means for pulling said air with vapors through said void,
   c) a first conductive layer means along one side of said void forming a common return for signals at particle resonant frequencies of one or more said particles,
   d) one or more second layer segment means located along the other side of said void for sending and receiving signals at particle resonant frequencies of one or more of said particles,
   e) Means for pinging each said segment at said resonant frequency of a particle of one of said vapors with a voltage signal,
   f) means of receiving a return ring signal from particles which were pinged,
   g) means for measuring the amplitude of said return signal,
   h) means for entering and storing tables of said amplitudes for mixes of interest of said vapors and air, and
   i) means for comparing said measured amplitudes of rings with said tables of amplitudes and outputting the probable amount present in the air sample of each said vapor of interest.

2. A method of detecting vapors mixed with air, said method consisting of the steps of:
   a) providing a multilayered printed circuit board with a void between layers forming a path for passing a thin layer of vapors mixed with air,
   b) fastening a fan to said board so as to draw vapors mixed with air through said void,
   c) providing a foil layer along a first side of said void as a return path for voltage waves oscillating at molecular resonant frequencies of particles making up said vapors,
   d) providing one or more electrically separated foil segments along the opposing second side of said void corresponding to one or more particles to be detected,
   e) pinging each said foil segment with a voltage signal at the mechanical resonant frequency of a particle to be detected,
   f) measuring the voltage ring produced by the particle immediately following said ping, and
   g) determining the number of particles contained in a given volume of air passing each said segment in a given length of time.

3. A device for measuring amounts of a single selected vapors mixed with air comprising in combination:
   a) A multilayered printed circuit board means having a void along an inner layer for air with vapors to pass through,
   b) fan means for pulling said air with vapors through said void,
   c) a first conductive layer means along one side of said void forming a common return for signals at particle resonant frequencies of one said particle,
   d) one second layer segment means located along the other side of said void for sending and receiving signals at particle resonant frequencies of one of said particles,
   e) Means for pinging the said segment at said resonant frequency of the selected particle of one vapor with a voltage signal,
   f) means of receiving a return ring signal from the particles which were pinged,
   g) means for measuring the amplitude of said return signal,
   h) means for entering and storing tables of said amplitudes for said vapor and air, and
   i) means for comparing said measured amplitudes of rings with said tables of amplitudes and outputting the probable amount present in the air sample of the said vapor of interest.

4. A method of detecting one vapor of interest mixed with air, said method consisting of the steps of:
   a) providing a multilayered printed circuit board with a void between layers forming a path for passing a thin layer of vapors mixed with air,
   b) fastening a fan to said board so as to draw vapors mixed with air through said void,
   c) providing a foil layer along a first side of said void as a return path for voltage waves oscillating at molecular resonant frequencies of particles making up said vapors, d) providing one electrically separated foil segments along the opposing second side of said void corresponding to one or more particles to be detected, e) pinging said foil segment with a voltage signal at the mechanical resonant frequency of the particle to be detected, f) measuring the voltage ring produced by the particle immediately following said ping, and g) determining the number of particles contained in a given volume of air passing each said segment in a given length of time.

5. A method as in claim 4 further including the steps of:

a) varying the air flow speed to find a speed of maximum efficiency, b) varying the length of the ping to find the length of maximum efficiency, c) varying the frequency of the ping to find the frequency of maximum efficiency, and d) repeating steps a) b) and c) in random orders to find overall conditions of maximum efficiency.

* * * * *